Sept. 6, 1960 J. A. HERHOLDT Plant Pat. 1,970
ROSE PLANT
Filed March 18, 1959
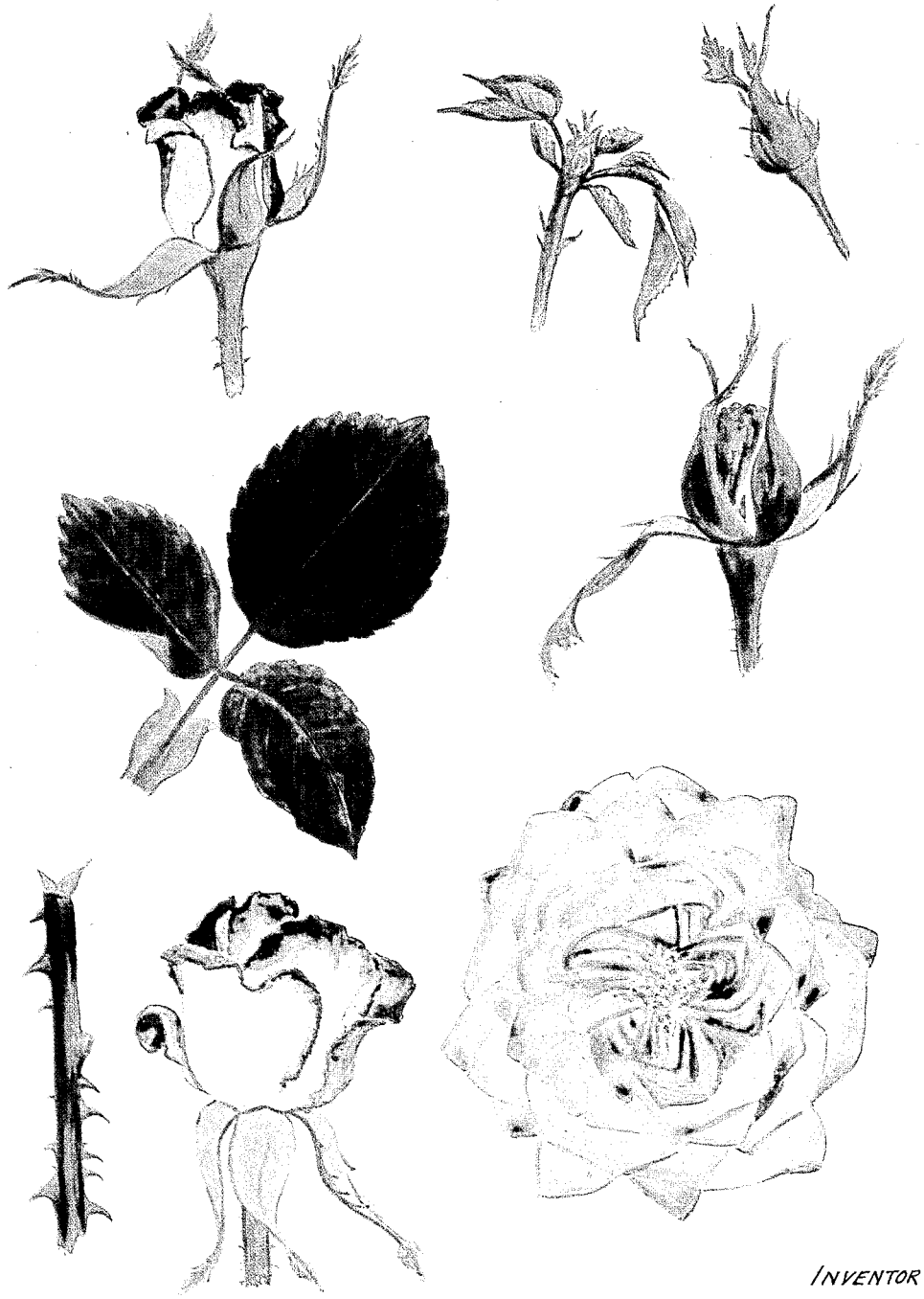
INVENTOR
JAN A. HERHOLDT
BY Irwin S Thompson
ATTY.

United States Patent Office

Plant Pat. 1,970
Patented Sept. 6, 1960

1,970

ROSE PLANT

Jan A. Herholdt, Heil-en-Lof, Eikenhof, Transvaal, Union of South Africa

Filed Mar. 18, 1959, Ser. No. 800,352

Claims priority, application Union of South Africa Mar. 24, 1958

1 Claim. (Cl. 47—61)

This invention relates to a new and distinct variety of rose plant belonging to the hybrid tea class, with full, double flowers, of creamy-white colour, flushed magenta-pink towards the edges of the petals and sweetly scented. The blooms are carried on long stiff stems which hold the flowers erect. It is of distinct colour, thus far not known in roses. An ideal rose for cutting and for beautification of out of doors gardens and parks.

In order to obtain the rose plant having the characteristics mentioned above, two roses were crossed. That chosen as the female (seed parent) is known as Peace (Plant Patent Number 591). That chosen as the male (pollen parent) was then an unnamed seedling rose, but has since been named Exciting, unpatented.

From this controlled pollination, many fruits were formed from which seeds were extracted whose cells were biologically different from those that would have come out of a natural self-pollination, due to the fact that they were the result of the union of the cells taken from different parents.

After sowing of the seeds the applicant obtained several small plants, physically and biologically different from one another.

These plants did not all correspond to the characteristics desired, and those that did not answer to the object of this research were eliminated. To further the experiments of these seedlings and to make sure of the stability of their characteristics, an "eye" with a vegetative capacity of each of the remaining seedlings was budded on to a suitable "root stock."

A few months later rose plants were obtained of good vitality and well-developed vegetation.

During two further years the systematic study of the distinct characteristics presented by the plants on trial led to the progressive elimination of all other budded varieties except a single one which corresponded to the qualifications sought for.

This rose plant produced vigorous growth with fine glossy foliage highly resistant to disease and produced flowers of excellent quality, perfect in form and of startling distinct colour of creamy-white, flushed light-red to magenta-pink towards the edges of the petals.

This positive result was good reason for considering whether this rose plant would be of merit to the horticultural industry. Tests were carried out which were conclusive of this new rose plant with a view to using it in the horticultural industry for the ornamentation of gardens and parks and also cut flowers for decoration.

The characteristics and properties of this new rose plant indicated above are thoroughly transmissible by "asexual" reproduction which will ensure its perpetuation, absolutely identical to that which is the subject of this patent.

As a result of this breeding, the applicant produced a new variety that is distinctly different from its parents, as well as from any other known variety of hybrid tea rose.

The plant of the new hybrid tea rose is of vigorous growth, and it blooms almost uncreasingly throughout the summer months. The blooms are carried on stiff stems which makes it a suitable cut rose. The buds are firm and well-formed. The bloom keeps its colour well in all weathers without fading until the petals drop.

Asexual reproduction of the new variety at "Heil-en-Lof," Eikenhof, Transvaal, South Africa, shows that the foregoing characteristics come true to form and are established and transmitted through succeeding propagations.

The method of reproduction used consisted in the budding of eyes from the seedling on to suitable root stocks.

The accompanying photographs show specimens of the new variety, with the flowers and foliage in different stages of development.

The following is a detailed description of the new variety, with colour terminology in accordance with Hickethier colour system and colour terms of ordinary dictionary significance:

*Description*

Class: Hybrid tea.

Plants:

*Height.*—3′ to 4′.
*Habit.*—Erect, upright branching.
*Growth.*—Vigorous.
*Canes.*—Medium to heavy.

Branches:

*Colour.*—Young shoots—greenish-red (Plate 746) shading to 767 at base of young shoots. Mature wood—light green (Plate 847).
*Prickles.*—Very sharp, only slightly recurved broad at base. Colour: on young shoots—purplish red (Plate 766) tipped with greenish yellow; on mature wood—straw coloured (Plate 311). Size—medium. Quantity—moderate in number, more frequent on vigorous branches.

Leaves:

*Stipules.*—Of medium size, adnate, green.
*Leaflets.*—Usually 5 in number, sometimes 3 or 7.
*Shape.*—Ovate, apex acute.
*Teeth.*—Serrations marked and irregular.
*Length.*—On an average 2¼″.
*Width.*—On an average 1⅜″.
*Colour.*—Young leaves—purplish green (Plate 855) with purple colouring more marked on the undersurface. Mature leaves—midgreen (Plate 847).
*Texture.*—Thick, leathery, glossy, with numerous prickles on undersurface of midrib.
*Foliage.*—In general the foliage is moderately abundant.

Inflorescence:

*Number of flowers.*—One bloom to a stem.
*Peduncle.*—Reddish-green (Plate 744) firm, with numerous small prickles from 2½″ to 3″ long, holds the flower erect.

Flower:

*Bud.*—Shape—elongated, pointed, firm, well-formed. Colour—outside creamy-white (Plate 100) margined soft pink (Plate 160) showing a richer shade on the petal surface, magenta-pink (Plate 483).
*Form.*—Very full, pointed, well-formed.
*Opening.*—Opens well, with petals folded backwards.
*Diameter.*—3½″ to 4″.
*Reference type.*—Entirely different to any existing variety known to applicant.
*Lasting qualities.*—Roses on the plant last exceptionally well in all weather conditions, 8–10 days from the opening of the bud. Cut blooms kept at living room temperature last from 5 to 6 days in water.
*Fragrance.*—Remarkably sharp, sweet fragrance.
*Calyx.*—Colour—light green with red (Plate 734), medium length, pointed; 5 sepals.

*Corolla.*—40–100 petals, very persistent.

*Petals.*—Texture—durable and petals of good thickness. Shape—roundish with apex, usually smooth edged, occasionally with one or two notches. Colour—outer petals pale creamy-white (Plate 100) tinted soft pink towards the edges (Plate 131) at apex bordered plate yellow (Plate 300). Inside surface of velvety texture, milky-white colour (Plate 100), about half of the petal flushed magenta-pink (Plate 483), towards the edges which intensifies in the full open flower to a deeper shade (Plate 493).

Reproductive organs:

*Stamens.*—45–60, many of which are either petalloid or filamentous staminodes; there are very few perfect stamens.

*Anthers.*—Vary in size, showing all gradations from normal anthers of medium size to extremely small degenerate anthers and even completely missing anthers.

*Filaments.*—Medium to short, curved, length varies from ½" to ⅛", tinted purplish-red (Plate 363).

*Pistils.*—60 to 70 in number.

*Pollen.*—Very little, colour brownish-red (Plate 943).

*Stigmas.*—Normal, yellow.

*Styles.*—Free, medium long, pubescent, white becoming purplish-red towards tip (Plate 374). Sometimes intertwined.

*Receptacle.*—Rounded, somewhat funnel-shaped.

*Fruit.*—Spherical, with seeds not completely enclosed.

*Aptitude for fruiting.*—Good, above the average.

Development:

*Blooming period.*—From spring until frost.

*Aptitude for recurrent blooming.*—Good, blooms throughout the summer months.

*Vegetation.*—Vigorous, upright branching.

*Disease resistance.*—Resistant to mildew and black spot as determined by comparison with other varieties of the same class grown under comparable conditions at "Heil-en-Lof," Eikenhof, district Vereeniging, Bosfontein, Maahaarrand, district Rustenburg.

This description was made from rose blooms out doors which were open for two or more days, in the month of December at "Heil-en-Lof," Eikenhof, Transvaal.

I claim:

A new and distinct variety of rose plant of the hybrid tea class as herein shown and described characterized as to novelty by full, double blooms, of creamy-white colour, flushed magenta-pink towards the edges of the petals, the sweet scent of the blooms and the fact that the blooms are carried on long stiff stems that hold them erect.

No references cited.